US007582072B2

(12) United States Patent
McMichael

(10) Patent No.: US 7,582,072 B2
(45) Date of Patent: Sep. 1, 2009

(54) ARTIFICIAL STOMA AND METHOD OF USE

(75) Inventor: Donald J. McMichael, South Jordan, UT (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 58 days.

(21) Appl. No.: 10/937,483

(22) Filed: Sep. 9, 2004

(65) Prior Publication Data

US 2006/0052752 A1 Mar. 9, 2006

(51) Int. Cl.
*A61M 5/32* (2006.01)

(52) U.S. Cl. ...................................................... 604/174

(58) Field of Classification Search ......... 604/174–175, 604/910, 104–108, 158, 116–117, 264
See application file for complete search history.

(56) References Cited

U.S. PATENT DOCUMENTS 3,752,162 A 8/1973 Newash
3,815,608 A 6/1974 Spinosa et al.
4,265,244 A 5/1981 Hill
4,666,433 A 5/1987 Parks
4,668,225 A * 5/1987 Russo et al. ................ 604/270
4,685,901 A 8/1987 Parks
4,701,163 A 10/1987 Parks
4,798,592 A 1/1989 Parks
4,834,712 A 5/1989 Quinn et al.
4,850,953 A 7/1989 Haber et al.
4,863,438 A 9/1989 Gauderer et al.
4,944,732 A 7/1990 Russo
4,986,810 A 1/1991 Semrad
5,007,900 A 4/1991 Picha et al.
5,071,405 A 12/1991 Piontek et al.
5,084,014 A 1/1992 Picha et al.
5,098,378 A 3/1992 Piontek et al.
5,125,897 A 6/1992 Quinn et al.
5,125,916 A 6/1992 Panebianco et al.
5,273,529 A * 12/1993 Idowu ........................ 604/500
5,308,325 A 5/1994 Quinn et al.

(Continued)

FOREIGN PATENT DOCUMENTS

EP 0853937 A1 7/1998

(Continued)

*Primary Examiner*—Nicholas D Lucchesi
*Assistant Examiner*—Theodore J Stigell
(74) *Attorney, Agent, or Firm*—Sue C Watson; Scott B Garrison; William W. Letson

(57) ABSTRACT

A device for creating a channel between the stomach lumen and the abdominal surface of a patient. The device includes a tube and a first bolster. The tube has a proximal end, a distal end, and a wall, the wall having an inner surface and an outer surface, and each end having an opening therein. The first bolster is attached to the distal end of the tube and the tube is adapted to slidably receive a feeding device having a shaft, wherein at least a portion of the outer diameter of the shaft of the feeding device is substantially the same size as that of the inner wall of the tube. The first bolster is adapted to sealingly engage with the patient so as to minimize or avoid fluid leakage about the tube. The present invention is also directed to a method of using an artificial stoma.

7 Claims, 3 Drawing Sheets

U.S. PATENT DOCUMENTS

| | | | | | |
|---|---|---|---|---|---|
| 5,342,321 | A | | 8/1994 | Potter | |
| 5,356,391 | A | | 10/1994 | Stewart | |
| 5,391,159 | A | | 2/1995 | Hirsch et al. | |
| 5,413,565 | A | | 5/1995 | Michels et al. | |
| 5,458,583 | A | | 10/1995 | McNeely et al. | |
| 5,527,280 | A | * | 6/1996 | Goelz | 604/99.02 |
| 5,555,898 | A | | 9/1996 | Suzuki et al. | |
| 5,720,734 | A | | 2/1998 | Copenhaver et al. | |
| 5,738,661 | A | | 4/1998 | Larice | |
| 5,860,952 | A | | 1/1999 | Quinn | |
| 5,871,467 | A | | 2/1999 | Reuning et al. | |
| 5,891,113 | A | | 4/1999 | Quinn | |
| 5,910,128 | A | | 6/1999 | Quinn | |
| D418,220 | S | | 12/1999 | Picha et al. | |
| 5,997,503 | A | | 12/1999 | Willis et al. | |
| 5,997,546 | A | | 12/1999 | Foster et al. | |
| 6,019,746 | A | * | 2/2000 | Picha et al. | 604/175 |
| 6,030,361 | A | | 2/2000 | Miyashiro | |
| 6,039,714 | A | * | 3/2000 | Cracauer et al. | 604/174 |
| 6,231,549 | B1 | | 5/2001 | Noecker et al. | |
| 2003/0163119 | A1 | * | 8/2003 | Chu et al. | 604/533 |

FOREIGN PATENT DOCUMENTS

| | | | |
|---|---|---|---|
| WO | WO 00/40289 | A2 | 7/2000 |

* cited by examiner

ARTIFICIAL STOMA AND METHOD OF USE

Numerous situations exist in which a body cavity needs to be catheterized to achieve a desired medical goal. One relatively common situation is to provide nutritional solutions or medicines directly into the stomach or intestines. Where nutritional solutions or medications need to be provided for extended periods of time, it is not uncommon to utilize an enteral feeding catheter which is placed through an opening in the patient's abdominal wall and stomach. Feeding solutions can then be injected through the catheter to provide nutrients directly to the stomach or intestines (known as enteral feeding).

A variety of different catheters intended for enteral feeding have been developed over the years, including some having a "low profile" relative to the patient during use and those having the more traditional or non-low profile configuration.

Enteral tubes for providing food and medication to a patient are well known. For example, U.S. Pat. No. 4,666,433, entitled Gastrostomy Feeding Device, invented by Parks and issued May 19, 1987; U.S. Pat. No. 4,701,163, entitled Gastrostomy Feeding Device, invented by Parks and issued Oct. 20, 1987; U.S. Pat. No. 4,798,592, entitled Gastrostomy Feeding Device, invented by Parks and issued Jan. 17, 1989; and U.S. Pat. No. 4,685,901, entitled Gastro-Jejunal Feeding Device, invented by Parks and issued Aug. 11, 1987 disclose earlier feeding tubes.

However, many of the catheters on the market today are commonly referred to as "replacement" catheters since they are substituted for an enteral feeding tube that is initially placed in a patient for six to eight weeks until a fistulas stoma tract is established. Once the stoma tract is established, the initial placement device is generally removed, and the "replacement" enteral feeding device is inserted into the stoma tract.

In use each of these catheters or at least the outer component thereof would come in contact with the patient and specifically the stoma site. A number of difficulties or problems are associated with the stoma site-catheter contact. For instance when the head of a catheter is pulled and/or twisted or the like, the body of the catheter in contact with stoma typically exerts some of the translated forces onto the patient. Numerous exertions can cause irritation of the stoma site.

It will further be appreciated that during this initial period the stoma site is often times tender and sensitive to movement of the catheter therein while healing and forming.

The process of establishing a stoma and enteral feeding is further complicated by swelling at the stoma site, which often times can be quite significant. As would be expected, as the swelling or inflammation decreases a catheter which was originally selected may no longer be properly sized thereby leading to undesirable catheter slippage or sliding within the patient.

That is, when a patient has an enteral feeding tube or catheter initially placed, it is common for the patient to experience some swelling or inflammation about the stoma site. As the stoma site begins to heal and swelling is reduced the catheter which was sized for the original, swollen dimensions of the stoma site may no longer be properly sized and/or may not have the ability to restrict slippage or sliding within or movement relative to the patient and thus can cause irritation to the patient, delay healing of the stoma site, or necessitate a new catheter. Such issues are further exacerbated with low profile devices because they are generally much more stoma or stoma site depth dependent than non-low profile devices.

Furthermore, there is frequently a desire of clinicians to include a jejunal feeding tube at the time of initial placement. The inclusion of a jejunal tube has in the past significantly complicated matters in that while jejunal feeding is desired, such a jejunal tube or lumen must either be inserted through a separate stoma site or through a PEG-type device. Clearly a second stoma site is undesirable. The alternative, however, is also undesirable, in that either a jejunal tube having a small lumen must be utilized in order to pass through the PEG style tube and still allow for gastric feeding or venting between the jejunal tube and the inner wall of the PEG style tube, or a much larger stoma site must be created in order to accommodate the larger desired jejunal lumen size and still allow for gastric feeding or venting between the jejunal tube and the inner wall of the PEG style tube. The use of a smaller jejunal tube may necessitate longer feeding times and disruption of the patient's activities, and/or the jejunal tube through the g-tube may only allow flow characteristics which are less than desired or intended. Of course a larger stoma site creates or provides additional obstacles or difficulties.

Additional difficulties associated with initial placement of catheters include, but are not limited to, the stoma site attempting to heal and close and exerting lateral or inward pressure or load on the catheters. Depending on the size of the stoma site, the size of the catheter, and the material the catheter is made of, the catheter may succumb to such pressure and at least partially collapse thereby further restricting the available flow path for gastric and/or jejunal lumens.

Further still, many initial placement devices are not readily removable without additional invasive surgical procedures. That is, many initially placed enteral catheters contain rigid retention members which cannot readily be passed through the stoma of the patient when it is desired to remove the initially placed device. Frequently, another endoscopic procedure is required to remove the initially placed device and/or to cut the distal end of the initially placed device so as to allow removal of the remainder of the device through the stoma. Accordingly, the distal end of an initially placed device which is cut from the device must either be extracted from the patient or allowed to pass through the patient's gastrointestinal tract, either of which can be traumatic to the patient.

There is a need and desire for a device which may be used during initial placement or creation of a stoma site and which offers sufficient rigidity to avoid succumbing to lateral loads the stoma site may exert on it. There is the need and desire for a device which reduces or minimizes the trauma associated with movements of a enteral feeding catheter within a stoma site. There is a further need and desire for a device which may be used for initial placement which can be adjusted to ensure desired positioning thereof is maintained as the swelling resulting from the initial placement subsides. There is also a need and desire to provide a device which maintains a desired stoma diameter size during patient healing following initial placement of a feeding tube yet and reduces or minimizes the irritation to the stoma during the period of healing. There is a need and desire for a device which is traction removable and does not require an invasive procedure nor does it require a patient to pass the end of a device which has been cut off or otherwise removed.

SUMMARY OF THE INVENTION

In response to the difficulties and problems discussed above, an artificial stoma has been developed.

One aspect of the present invention is directed to a device for creating a channel between the stomach lumen and the abdominal surface of a patient. The device includes a tube and a first bolster. The tube has a proximal end, a distal end, and a wall, the wall having an inner surface and an outer surface, and each end having an opening therein. The first bolster is attached to the distal end of the tube and the tube is adapted to slidably receive a feeding device having a shaft, wherein at least a portion of the outer diameter of the shaft of the feeding device is substantially the same size as that of the inner wall of the tube. The first bolster is adapted to sealingly engage with the patient so as to minimize or avoid fluid leakage (e.g., stomach fluids or the like) about the tube. Numerous variations of such a device are contemplated, including one where the first bolster is a bumper. In some aspects the bumper may be of a design which allows the bumper to fold in a predetermined manner. Other aspects of the present invention may also include a second bolster, the second bolster being adapted to facilitate maintaining the position of the device within the patient. The second bolster may include a spring clip to engage with the outer wall of the tube to assist in maintaining the positioning of the device. The second bolster may also include an attachment mechanism to secure the feeding device thereto. The attachment mechanism of the second bolster may be adapted to be secured to a head of the feeding device. The attachment mechanism may be adapted for rotational engagement with the feeding device.

The present invention is also directed to a method of using an artificial stoma. The method may include the steps of providing an artificial stoma, such as that, described above, having a tube and a first bolster. The tube has a proximal end and a distal end, and a wall, the wall having an inner surface and an outer surface, and each end having an opening therein. The first bolster being attached to the distal end of the tube. The tube being adapted to slidably receive a feeding device having a shaft, wherein at least a portion of the outer diameter of the shaft of the feeding device is of sufficient size so as to prevent or minimize liquid flow between the feeding device and the inner wall of the tube. The first bolster is also adapted to sealingly engage with the patient, and more specifically the abdominal cavity of a patient. The method also includes the steps of positioning the artificial stoma within a patient such that a proximal edge of the first bolster contacts the patient adjacent a stoma site through which the tube is to be placed so as to minimize or avoid fluid leakage about the tube; providing a feeding device having a shaft wherein the portion of the shaft which is to be slidingly received through the tube is smaller than the dimensions of the inner wall of the tube, and wherein at least a portion of the outer diameter of the shaft of the feeding device which is to be positioned within the tube is of sufficient size so as to minimize or prevent liquid flow through the tube about the feeding device; and inserting the feeding device through the tube into a predetermined position within the patient.

The method of the present invention may further include the steps of providing a second bolster on the tube, the second bolster being adapted to facilitate maintaining the position of the tube within the patient; and positioning the bolster about the tube so as maintain the tube within the patient in a desired position. The second bolster may further include an attachment mechanism to secure the feeding device thereto; and the method may include the step of securing the feeding device to the attachment mechanism so as to retain the position of the feeding device relative to the second bolster. The step of positioning the artificial stoma may, be done via any suitable procedure or device including for example a "trocar" type insertion sleeve or via percutaneous endoscopic gastrostomy placement.

The invention will be more fully understood and further features and advantages will become apparent when reference is made to the following detailed description of exemplary aspects of the invention and the accompanying drawings.

BRIEF DESCRIPTION OF THE DRAWINGS

The purpose and advantages of the present invention will be apparent to those skilled in the art from the following detailed description in conjunction with the appended drawings in which.

DETAILED DESCRIPTION OF THE PRESENT INVENTION

Reference will now be made in detail to one or more examples of the invention depicted in the figures. Various elements of the present invention will be given numeral designations and the invention will be discussed so as to enable one skilled in the art to make and use the invention. It should be appreciated that each example is provided by way of explaining the invention, and not as a limitation of the invention. For example, features illustrated or described with respect to one aspect may be used with another aspect to yield still a further aspect. These and other modifications and variations are contemplated to be within the scope and spirit of the invention.

In addition, the invention will be described in the context of its various configurations. It should be appreciated that alternative arrangements of the invention can comprise any combination of such configurations. As such, the use of a desired aspect for ease in understanding and describing the invention shall not, in any manner, limit the scope of the invention.

For ease in understanding, the following detailed description will be made in the context of an artificial stoma which is adapted for use with enteral feeding tubes, catheters, or the like. It should be appreciated that, although the present invention has particular usefulness with enteral feeding tubes and catheters, the invention is not limited in scope to feeding tubes or the medical industry. An artificial stoma according to the present invention has wide application and can be used in any instance wherein there is a need to link a cavity to another cavity or open area when there is a barrier in between. All such uses and applications are contemplated within the scope of the invention. An exemplary use would be a device for creating a channel between the stomach lumen and the abdominal surface of a patient.

As used herein, the term "distal" generally refers to the direction of the patient or the end of a device intended to be closest to or inserted the farthest into a patient and the term "proximal" generally refers to the direction of the clinician or the end of a device intended to be furthest from or inserted the least into a patient.

Figure 2:
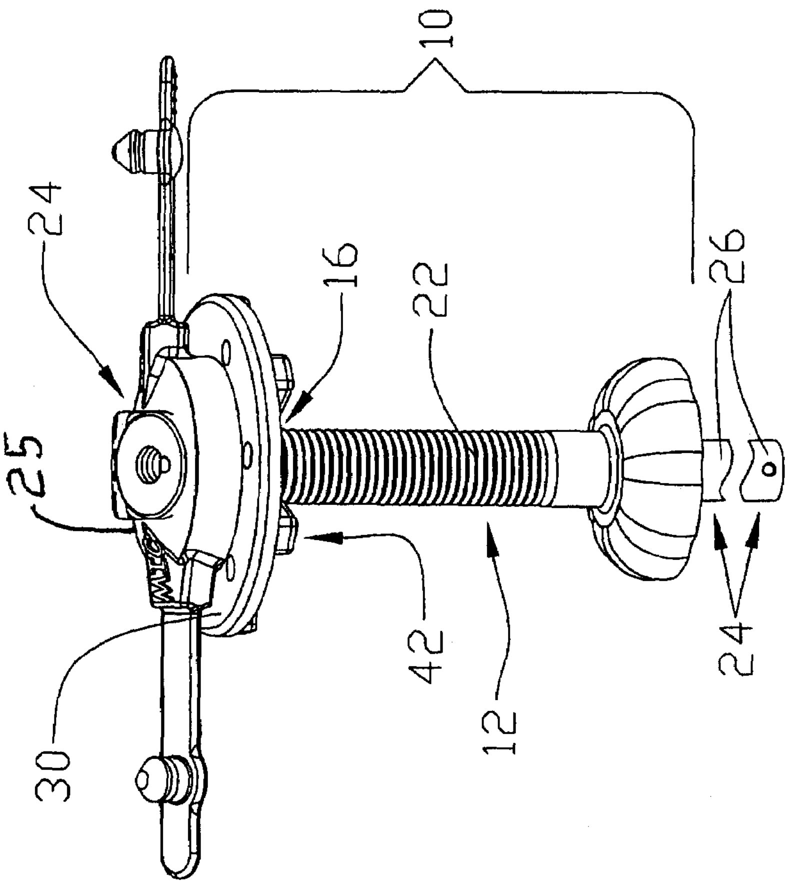
FIG. 2 is a elevated side view of an artificial stoma according to an aspect of the present invention, the artificial stoma shown with a catheter passed therethrough.
Figure 1:
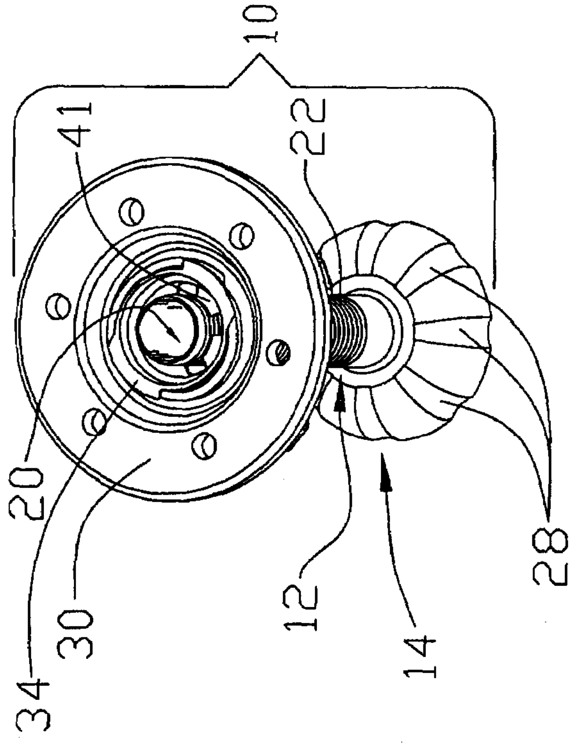
FIG. 1 is an oblique view of an aspect of an artificial stoma according to the present invention.
Figure 4:
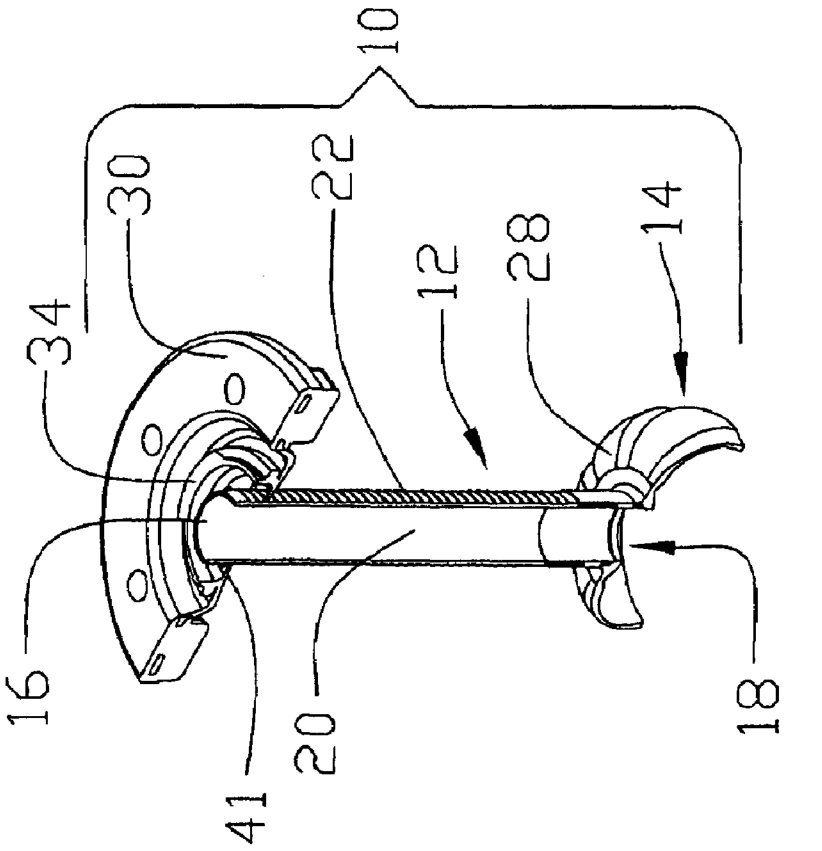
FIG. 4 is the elevated cross-sectional view of the artificial stoma of FIG. 3 without the catheter therethrough.
Figure 3:
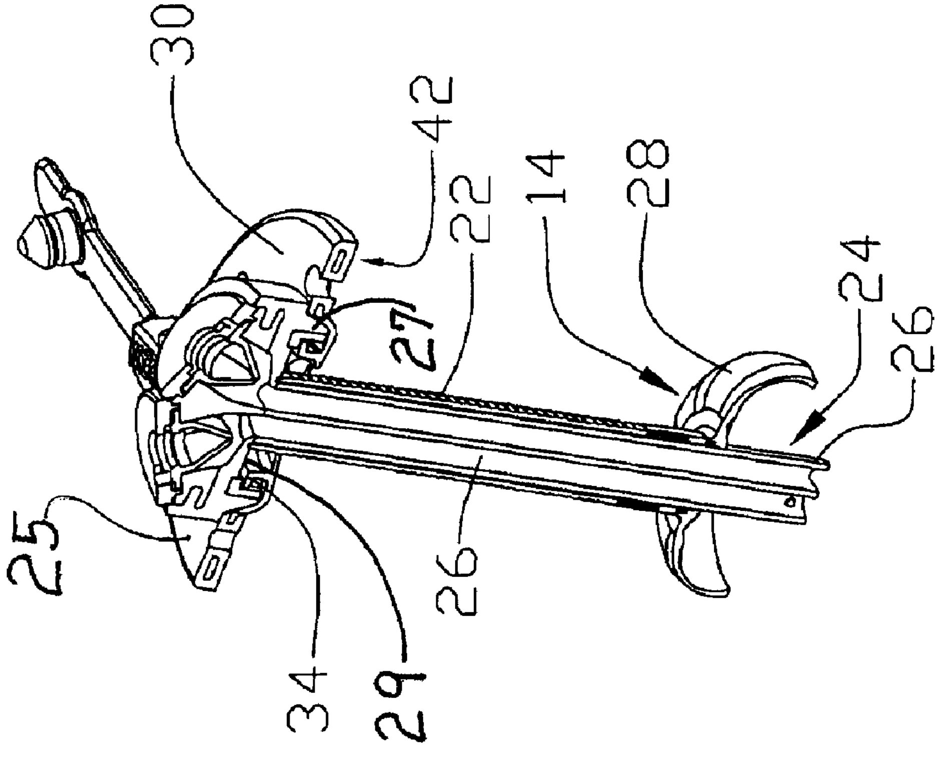
FIG. 3 is a cross-sectional view of an artificial stoma according to an aspect of the invention with a catheter passed therethrough.
Figure 5:
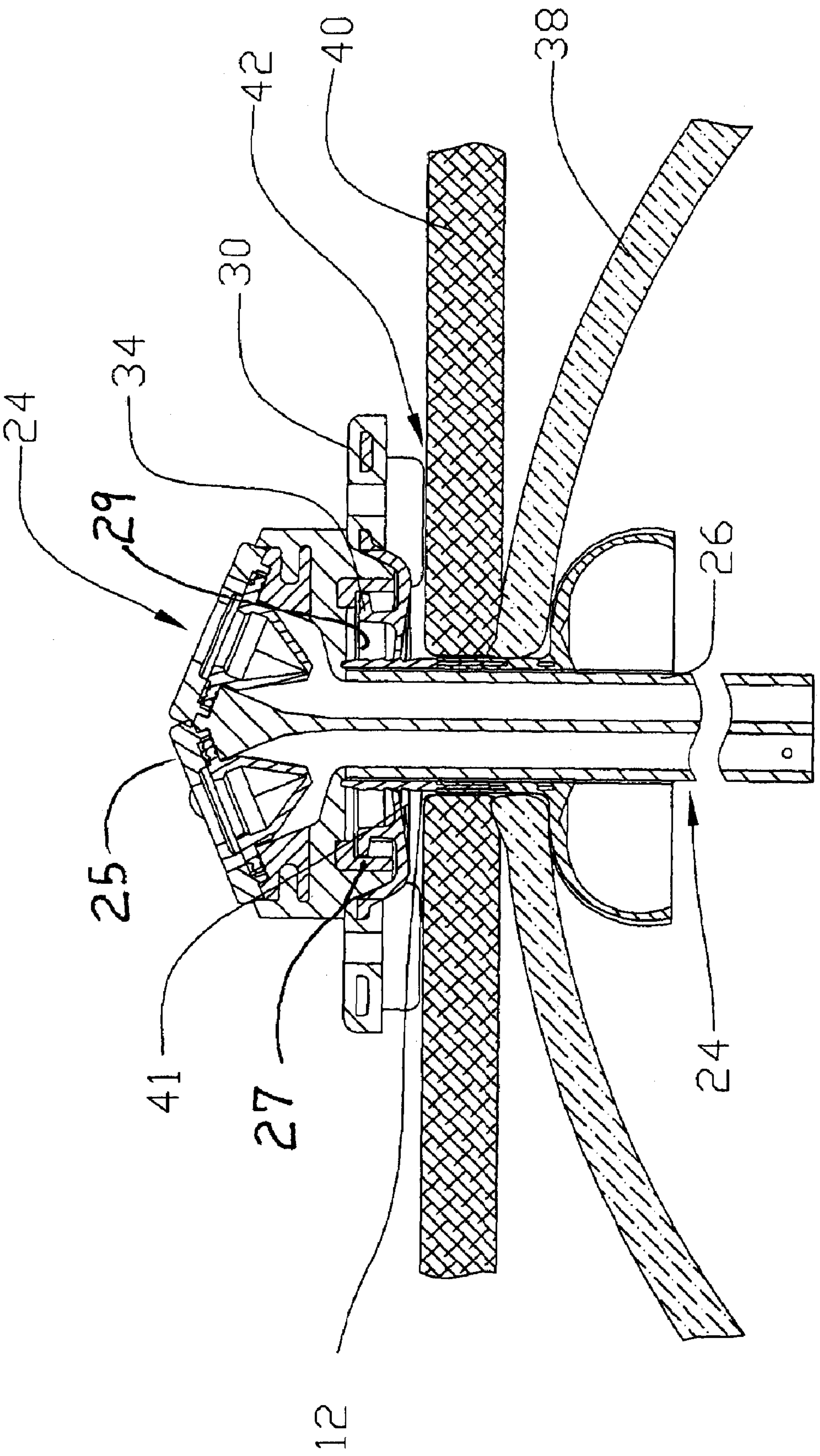
FIG. 5 is a cross-sectional view of an artificial stoma according to an aspect of the present invention with a catheter positioned therethrough, wherein the artificial stoma is positioned within the patient.

FIG. 1 illustrates an artificial stoma 10 according to the invention. Such an artificial stoma has wide application and, while the invention may useful in enteral feeding applications, the invention can be used in any instance where it is desirable to link a cavity to a cavity or a cavity to an open area. The artificial stoma 10 illustrated includes a tube 12 and a first bolster 14. The tube 12 is shown having a proximal end 16 and a distal end 18, and a wall, the wall having an inner surface 20 and an outer surface 22. Each end of the tube having an opening therethrough. The first bolster 14 is shown attached to the distal end 18 of the tube 12. The tube 12 is adapted to slidably receive a feeding device 24 (such as that illustrated in FIG. 2) having a shaft 26, wherein at least a portion of the outer diameter of the shaft 26 of the feeding device 24 is substantially the same size as that of the inner wall 20 of the tube 12. The first bolster 14 is also adapted to sealingly engage with the patient, and more specifically the abdominal cavity of a patient, so as to minimize or avoid fluid leakage about the tube 12.

A number of enteral feeding catheters are known to exist, and although some of them are know to include a feeding tube within a feeding tube, the outer tube of prior devices is still used for feeding and/or drainage, can become clogged or blocked and must be replaced from time to time. Unlike the prior devices the tube 12 is not designed to be used for the transmission of fluids, namely nutritional supplements and the like. Rather, the tube 12 of the artificial stoma 10 is designed to protect the patient and the stoma site from the forces which might otherwise be exerted thereon by a feeding tube, as well as to serve as a channel which facilitates passage and removal of the feeding tubes themselves. If the proper size feeding tube or catheter is selected for use with the device of the present invention (or vice versa), then no fluids are designed to be passed about or between a feeding tube which may be passed therethrough and the inner wall of the device of the present invention.

In one aspect of the invention the first bolster may be a bumper 14 as shown in FIGS. 1-5. The bumper 14 may be attached to the distal end 18 of the tube 12 in a variety of acceptable manners, but it has been found that attachment by way of overmolding is reliable and produces suitable results. The bumper is desirably resilient so as to be able to maintain or assist in the maintenance of the positioning of the artificial stoma 10, yet is also sufficiently flexible to allow for traction removal of the device. As will be discussed in more detail below, the bumper 14 may be of a specific design so as to allow the bumper to fold in a predetermined manner in order to facilitate insertion with a trocar-style instrument and/or to facilitate removal of the device. As suggested above, any suitable bumper shape or configuration is contemplated. One suitable bumper shape is a domed bumper such as that illustrated in FIGS. 1 and 2. As illustrated, the bumper 14 may be webbed and may include ridges or spokes 28 therein. The spokes 28 and webbing therebetween may be designed to fold in a predetermined and/or uniform manner so as to facilitate insertion or removal of the device 10. While the bumper 14 may be made of any suitable material, exemplary materials include silicone, polyurethane, and PVC.

Some aspects of the artificial stoma may include a second bolster 30 which in application is adapted to assist in maintaining the position of the artificial stoma within the patient, and more particularly to reduce or minimize sliding of the artificial stoma 10 into or inwards of the patient. The second bolster 30 should be designed so as to fit over a least a portion of the tube 12 of the artificial stoma 10 and such that the second bolster 30 may be moved or advanced toward the distal end 18 of the tube 12 so as to desirably contact the abdomen of the patient as suggested in FIG. 3. The second bolster 30 may work in combination with the first bolster 14 such that the stomach wall 38 and abdomen 40 are sandwiched therebetween. The second bolster 30 should be capable of being advanced toward the distal end 18 of the tube 12 such that a snug but not tight arrangement is achieved. The second bolster 30 may take many forms, including for example, a friction fit slidable ring such as the SECURE-LOK* ring available from Ballard Medical Products, a fully owned subsidiary of the assignee of the current invention. It will be appreciated that any configuration which will reduce or minimize undesired movement of the second bolster 30 and thereby avoid undesirable or excessive compression between the bolsters and/or undesirable loosening of the bolsters is suitable. Exemplary configurations of the second bolster 30 may further include grooves, threads, or the like with which the tube 12 may interact to further assist in maintaining the position of the second bolster 30 relative to the patient and the tube 12. The second bolster may also include a spring clip 41 (FIG. 2) or the like which engages the outer wall of the tube 12 and relatively easily permits movement or advancement in one direction, but does not readily permit movement in the opposite direction without destroying the spring clip or without significant effort relative to that needed to advance the bolster. Such a spring clip would be useful where the second bolster 30 would be advanced as swelling around the stoma site decreased and/or where the second bolster 30 was not anticipated to be removed or loosened until the artificial stoma 10 was intended to be removed from the patient.

Another feature contemplated to be included in one or more aspects of the present invention is an attachment mechanism, for example, a rib 34 on the second bolster 30 which may be used to secure a catheter or feeding device 24 to the second bolster 30. Such an attachment mechanism would be especially useful with low-profile feeding tubes and/or feeding tubes which do not include an internal retention member, such as a balloon or the like. Any variety of suitable attachment mechanisms are contemplated. Exemplary mechanisms include snap-fits, threaded engagement or other rotational engagement. It is contemplated for example where a threaded engagement mechanism is present, as illustrated in FIG. 1, that the catheter or feeding device 24 would be rotated in the direction of arrow 32 such that the bolster 30 and the head 25 of the catheter 24 were secured to one another, a rim 27 on a distal surface 29 of the head 25 releasably coupling to the attachment mechanism or rib 34 of the second bolster 30. It is of note that even where the tube 12 is shortened (i.e., cut off by a clinician at a desired height, or if the tube extends too far from the patient) the second bolster 30 can still be attached to the head 25 of the catheter or feeding device 24.

The present invention is also designed to overcome some of the difficulties associated with a catheter being placed in direct contact with a stoma site. Two problems in particular are addressed by or with the construction tube 12 of the artificial stoma 10, namely catheter collapse and stoma site irritation. More specifically, where a traditional feeding catheter is initially placed in a patient, there is a tendency for the stoma site to attempt to close during or as part of the healing process. Where traditionally soft and flexible feeding catheters are subjected to lateral forces by the patient's skin, it is common for the sidewalls of the catheter to become deformed resulting in less than maximum flow through one or more of the catheter's lumens. In some cases the flow through the catheter could be completely blocked. Even in those cases where the flow through the catheter is not restricted beyond a useful degree, there may be an issue with respect to the size of the stoma upon healing. That is, the stoma may be narrower than desired as the flexible walls of the catheter were not resilient enough to maintain a certain diameter stoma size. This may become an issue when a replacement catheter is attempted to be placed in the patient.

Yet another problem with initially placed catheters is that the contact between the catheter and stoma site can case irritation during use of the catheter. More specifically, during use of the catheter the head of the catheter is frequently subjected to a number of forces, especially during connection and disconnection of feed sets. These forces, including twisting and pulling are frequently translated in part to the stoma site. As one skilled in the art will appreciate, such forces can be particularly uncomfortable to a patient, and particularly so when the stoma site is healing and may be more sensitive or tender than once the stoma has formed. The ability to avoid or reduce the translation of such forces is a significant advantage over prior devices.

The present invention addresses each of theses issues by or with the tube 12. Specifically, the tube should be of resilient construction such that the lateral forces expected to be experienced by the stoma site wall will not result in collapse or deformation of a catheter passed therethrough. Any suitable material or materials may be used, although a tube that has some flexibility may provide more comfort to a patient than a hard tube. The selection of a tube which is resistant to collapse or deformation under the described conditions will also be able to maintain a specific stoma site size until the stoma is formed.

Further still, the tube 12 of the artificial stoma 10 of the present invention further allows for a reduction of the forces that are translated to or exerted on the stoma site by the catheter by eliminating direct contact between the catheter 24 and the stoma site. While some forces will inevitably still be experienced at the stoma site, the reduction is expected to be of significant benefit to the patient as discomfort is expected to be reduced and stoma site healing should be faster as less irritation and/or trauma is expected with the artificial stoma.

It is also of note that the tube 12 of the artificial stoma 10 is designed to function at variable lengths. The tube 12 is desirably of such construction, that while of sufficient rigidity or resiliency, it is also desirably of a material that may be readily trimmed or cut at the proximal end so that excessive material does not protrude unnecessarily from a patient, so as to hinder the patient or result in discomfort thereto. In some embodiments, the tube 12 may even be scored to facilitate such trimming or cutting.

The present invention is also directed to a method of using an artificial stoma. The method generally includes a number of steps including providing an artificial stoma, such as that described above, having a tube 12 and a first bolster 14. The tube 12 has a proximal end 16 and a distal end 18, and a wall, the wall having an inner surface 20 and an outer surface 22, and each end having an opening therein. The first bolster 14 being attached to the distal end 18 of the tube 12. The tube 12 being adapted to slidably receive a feeding device 24 (such as that illustrated in FIGS. 2, 3 and 5) having a head 25 and a shaft 26, wherein at least a portion of the outer diameter of the shaft 26 of the feeding device 24 is of sufficient size so as to prevent or minimize liquid flow between the feeding device 24 and the inner wall 20 of the tube 12. The first bolster 14 is also adapted to sealingly engage with the patient, and more specifically the abdominal cavity of a patient. The method also includes the steps of positioning the artificial stoma within a patient such that a proximal edge of the first bolster contacts the patient adjacent a stoma site through which the tube is to be placed so as to minimize or avoid fluid leakage about the tube; providing a feeding device having a head and a shaft wherein the portion of the shaft which is to be slidingly received through the tube is smaller than the dimensions of the inner wall of the tube, and wherein at least a portion of the outer diameter of the shaft of the feeding device which is to be positioned within the tube is of sufficient size so as to minimize or prevent liquid flow through the tube about the feeding device; and inserting the feeding device through the tube into a predetermined position within the patient.

At least one aspect of a method of the present invention may further include the steps of providing a second bolster 30 on the tube 12, the second bolster 30 being adapted to facilitate maintaining the position of the tube 12 within the patient, and positioning the bolster about the tube 12 so as maintain the tube 12 within the patient in a predetermined position. In some aspects of the present invention the second bolster 30 may further include an attachment mechanism such as rib 34 to secure the head 25 of the feeding device 24 thereto, and the method may further include the step of securing the head 25 of the feeding device 24 to the attachment mechanism or rib 34 so as to retain the position of the feeding device 24 relative to the second bolster 30.

The present invention is also directed to a method for providing a system of using an artificial stoma. The method includes the steps of: providing an artificial stoma 10 such as one of the embodiments described above, the device including a tube and a first bolster; providing directions for positioning the artificial stoma within the patient so that the edge of the first bolster contacts the patient adjacent a stoma site through which the tube is placed so as to minimize or avoid fluid leakage about the tube; and providing directions for inserting a feeding device through the tube into a predetermined position within the patient. The method could further include the step of providing directions to select a feeding device having a shaft wherein the portion of the shaft which is to be slidingly received through the tube is smaller than the dimensions of the inner wall of the tube, and wherein at least a portion of the outer diameter of the shaft of the feeding device which is to be positioned within the tube is substantially the size of the inner wall to minimize or prevent fluid flow through the tube about the feeding device.

While a number of variations are possible, the step of positioning the artificial stoma will generally be done in one of two ways. That is, either with a “trocar” type insertion sleeve, or via percutaneous endoscopic gastrostomy (PEG) style placement. More particularly with respect to the trocar type insertion sleeve, an opening in a patient’s abdomen and stomach wall may be created with a trocar or other conventional means such as a scalpel or the like. Once the opening is created a device (not shown) which fits over the tube 12 and bolster 14 of the artificial stoma 10 in a sleeve-like manner may be inserted into the opening. Once the distal end of the insertion device is within the stomach or other desired cavity within the patient the artificial stoma may be advanced or the sleeve withdrawn such that the bolster protrudes therefrom and then the insertion device or sleeve may be removed from the patient such that the artificial stoma is left in the patient. If the bolster is not already properly positioned against the stomach wall of the patient as desired, the artificial stoma may be adjusted until a desired position is achieved. With respect to the PEG style placement, the artificial stoma may be introduced into the patient by way of an endoscope and then passed through a stoma site (which has been created by conventional techniques) by advancing or pulling the proximal end of the tube therethrough. As with the trocar style placement, the artificial stoma may then be positioned against the stomach wall of the patient as desired.

Once the tube 12 of the artificial stoma 10 is in the predetermined or desired position, in those aspects where a second bolster 30 is included the second bolster should be positioned about the tube or secured to the tube 12 so as maintain the tube 12 within the patient in a predetermined position. It will be appreciated that it is desirable to retain the tube 12 such that the first bolster 14 attached thereon or thereto remains in contact with the inner wall of the cavity into which the tube 12 is inserted such that fluids do not leak from the patient about the tube 12. In order to maintain such positioning of the tube 12, it may be necessary to advance the second bolster 30 relative to the tube 12 and first bolster 14 such that the first bolster 14 is drawn against the inner wall of the cavity of the patient. One skilled in the art will appreciate that sufficient pressure may be maintained if the second bolster 30 is advanced or positioned such that there is a relatively snug, but not necessarily tight, fit between the proximal surface of the first bolster or bumper 14 and the inner wall of the cavity of the patient the artificial stoma 10 is inserted therein as well as between the distal edge or surface 42 of the second bolster 30 and the skin of the patient's abdomen 40. While some pressure may need to be asserted in order to prevent or minimize leakage, care should be taken to avoid excessive pressure as the excessive pressure may cause discomfort to the patient.

Once the second bolster 30, if present, is positioned the shaft 26 of the feeding device 24 which has been selected should be positioned within the tube 12 such that the distal end of the catheter or feeding device 24 extends from the tube 12. How far the distal end of the catheter or feeding device 24 extends from the tube 12 will depend in part on what type of catheter has been selected and/or if an internal retention member is present on the catheter. The selected artificial stoma 10 is designed to be used with a catheter or feeding device 24 such that the exterior of the catheter shaft 26 will readily slide within or through the tube 12, yet at least a portion of the catheter shaft that will be within the tube when positioned as desired will be substantially the size of the interior of the tube 12. That is, the selected catheter is designed to be just smaller than the inside diameter of the tube 12 such that catheter may pass therethrough yet still be of sufficient size to prevent or essentially prevent fluids from passing between the tube 12 and the catheter or feeding device 24. That is, the present invention does not contemplate the tube 12 functioning as a liquid transmission or venting lumen.

Depending on the catheter selected for use with the artificial stomas of the present invention, it may be necessary to activate a retention member on the catheter in order to maintain the catheter within the patient. Alternatively, the present invention also contemplates the second bolster 30 having an attachment mechanism 34 which may be used to maintain the position of a catheter with or without a separate retention member. Such an attachment mechanism is contemplated to be especially useful with or for low profile devices. The ability to be used with a low profile device is significant as traditionally it was difficult to use a low profile device as an initial placement device because of the swelling and inflammation around the stoma site and because low profile devices are traditionally selected based on the size and depth of a stoma tract. Thus, as is appreciated by those having skill in the art, heretofore, low profile devices had to be either selected for the initial stoma site depth and become loose as the swelling at the stoma site subsided or the device had to be selected for what was believed would be the depth after swelling subsided and discomfort to the patient would have to be a consequence of the initially tight fit.

The present invention overcomes the difficulties previously associated with the initial placement of a low profile device in a couple of ways. First, a second bolster can have an attachment mechanism configured to attach to a catheter, and more desirably the head of a low profile device. This attachment avoids the need for the catheter to possess a retention mechanism which is deployable within the patient and/or provides for the opportunity to maintain a low profile without slack or a loose fit being created between the patient and the head of the catheter as swelling at the stoma site reduces. For example, as the swelling about the stoma site subsides, the proximal end of the tube 12 may be shortened the clinician and the second bolster 30 may be advanced along the tube 12 towards the first bolster 14 until the second bolster is positioned against the skin of the patient. The head 25 of the low profile catheter or feeding device 24 may then be secured by way of the attachment mechanism 34 to the second bolster 30. It is contemplated that as the swelling at the stoma site decreases, that the catheter or feeding device 24 and second bolster 30 may be disconnected, the tube 12 shortened without necessitating removal of the catheter or feeding device 24, and then advancement of the bolster 30 (if necessary) and attachment or reattachment of the bolster 30 to the catheter or feeding device 24, as generally described above.

The present invention also allows a clinician to avoid using additional retention mechanisms, such as sutures or T-fasteners, which are well known in the art and which have traditionally been used to secure or retain a feeding catheter relative to a patient following initial placement.

While much of the discussion above is directed to placement and use of the artificial stoma, the artificial stoma of the present invention is also designed so as to desirably be able to extracted from the patient without the need for an additional surgical procedure. That is, as mentioned above, the first bolster 14 at or near the distal end 18 of the tube 12 is desirably constructed of one or more materials that are resilient enough to be able to maintain or assist in the maintenance of the positioning of the artificial stoma 10, yet is also sufficiently flexible to allow for traction removal of the device. As above, any suitable bolster design is contemplated, however, those which fold or collapse in a predetermined or at certain pressure thresholds are desirable to facilitate traction removal thereof. For instance, those bolsters that will that fold in a predetermined manner, especially those which fold or collapse so as not to have edges which protrude radially farther than the outer wall 22 of the tube 12 will provide for easier traction removal of the artificial stoma 10 at a desired time. A bolster designed to collapse under a certain amount of pressure will help ensure that the artificial stoma is maintained in position under normal circumstances, but will also allow the clinician to remove the device from the patient without needing to exert undue force on the patient or without knowing if the pressure being required to remove the tube from the patient is a result of the bolster or if the device is caught on or in the patient.

While the invention has been described in detail with respect to specific aspects thereof, those skilled in the art, upon obtaining an understanding of the invention, may readily conceive of alterations to, variations of, and equivalents to the described aspects and the processes for making them. The invention may be embodied in other specific forms without departing from the scope and spirit of the inventive characteristics thereof. The present aspects therefore are to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. A device for providing a channel between a stomach lumen and abdominal skin of a patient, the device comprising:

a relatively rigid protective tube constructed to resist deformation or collapse comprising a generally tubular wall having an outer surface, a proximal end and a distal end defining a length of the protective tube, and an opening in each end which extends through the protective tube to define an inner surface of the tubular wall, wherein the protective tube is configured to be positioned in a stoma extending between a stomach lumen and a patient's abdominal skin to provide a channel therebetween, wherein a portion of the protective tube is configured to be removed at the proximal end to reduce the length, and wherein the protective tube is not adapted for the transmission of fluids;

a first bolster provided adjacent to the distal end of the protective tube, the first bolster configured to be positioned against an internal wall of a patient's stomach such that when the distal end of the protective tube is positioned in a patient's stomach, the first bolster is configured to extend outward, away from the protective tube such that it is sealingly positioned against the internal wall so as to minimize or avoid fluid leakage through the stoma;

a second bolster provided adjacent the proximal end of the protective tube and configured to permit the protective tube to pass therethrough, the second bolster movable over the protective tube and configured to be secured to the protective tube to permit it to be positioned against the patient's abdominal skin, the second bolster having a proximal surface, a distal surface and an opening therethrough, the protective tube positioned through the opening of the second bolster such that when the distal end of the protective tube is positioned in the patient's stomach lumen and the first bolster is sealingly positioned against the internal wall of the stomach lumen, the second bolster is moved over the protective tube such that its distal surface is positioned against the patient's abdominal skin, wherein the second bolster is configured to maintain a position on the outer surface of the protective tube, and wherein the second bolster includes a spring clip which engages the outer surface of the protective tube such that the second bolster is maintained in the position, the second bolster configured to releasably couple to at least a portion of a feeding device; and a feeding device including a head and a shaft extending therefrom, the head and the shaft positioned in a perpendicular orientation relative to each other, the head including at least one opening formed therein in communication with an opening provided through the shaft, the head further including a distal surface configured to be positioned against and releaseably coupled to at least a portion of the proximal surface of the second bolster, and wherein when the feeding device is coupled to the second bolster, the head of the feeding device and the second bolster are positioned in a generally parallel alignment relative to each, the distal surface of the second bolster is positioned against the patient's abdominal skin and the shaft of the feeding device is positioned through the protective tube such that a distal portion of the shaft extends a distance from the distal end of the protective tube to provide transmission of fluids from the opening in the head, wherein the shaft is configured such that a substantial portion of an outer surface of the shaft is positioned against a substantial portion of the inner surface of the protective tube, and wherein a diameter of the substantial portion of the outer surface of the shaft slidably abuts a diameter of the substantial portion of the inner surface of the protective tube to prevent backflow of fluid through the protective tube when fluid is introduced to a patient's stomach via the opening in the head and the shaft of the feeding device.

2. The device of claim 1, wherein the first bolster is a bumper.

3. The device of claim 2, wherein the bumper is of a design so as to allow the bumper to fold in a predetermined manner.

4. The device of claim 1, wherein the second bolster further comprises an attachment mechanism on its proximal surface, and wherein the distal surface of the head of the feeding device cooperates with the attachment mechanism to releaseably couple the head to at least the portion of the proximal surface of the second bolster.

5. The device of claim 4, wherein the attachment mechanism includes a rib, and wherein the head of the feeding device cooperates with the rib to rotationally couple the head to the portion of the proximal surface of the bolster.

6. The device of claim 5, wherein the attachment mechanism is integrally formed with the second bolster.

7. The device of claim 1, wherein the second bolster does not include a valve.

* * * * *